United States Patent [19]

Saito et al.

[11] Patent Number: 4,794,450
[45] Date of Patent: Dec. 27, 1988

[54] METHOD AND APPARATUS FOR JUDGING AGGLUTINATION PATTERN

[75] Inventors: Tomo Saito; Yasusuke Sakurabayashi; Toshitsugu Inouchi; Norihiro Suzuki, all of Tokyo, Japan

[73] Assignee: Fujirebio Kabushiki Kaisha, Tokyo, Japan

[21] Appl. No.: 90,477

[22] Filed: Aug. 28, 1987

[30] Foreign Application Priority Data

Aug. 29, 1986 [JP] Japan .............................. 61-201779
Apr. 14, 1987 [JP] Japan .............................. 62-89785

[51] Int. Cl.⁴ ........................ H04N 7/18; G06K 9/00
[52] U.S. Cl. .................................. 358/93; 382/6; 364/413.01; 356/39
[58] Field of Search .................. 358/93, 107; 382/6; 356/39; 364/416; 377/10

[56] References Cited

U.S. PATENT DOCUMENTS 4,453,266  6/1984  Bacus ........................................ 382/6
4,702,595 10/1987  Mutschler et al. ................. 382/6 X
4,720,787  1/1988  Lipscomb ............................ 364/416

Primary Examiner—Howard W. Britton
Assistant Examiner—Victor R. Kostak
Attorney, Agent, or Firm—Sughrue, Mion, Zinn, Macpeak and Seas

[57] ABSTRACT

An apparatus for judging an agglutination has a transparent plate stand 5 for supporting a microplate 7 and perforated with positioning openings 9 for centering of each well 8 of the microplate. A light source and TV camera 12 are disposed above the microplate, an image memory 13 stores the output of the camera, a processor 15 differentiates the stored image to determine its profile, and the picture elements of the differentiated image having intensity levels larger than zero are counted. A calculator 17 produces coefficients of variation, which are plotted against the image profile and compared with a reference value to remove contrast irregularities.

5 Claims, 4 Drawing Sheets

|   | I | II | III | IV | V | VI |
|---|---|---|---|---|---|---|
| A | 51  3 | 49  4 | 48  2 | 47  7 | 45  3 | 44  9 |
| B | 49  7 | 47  8 | 45  9 | 43  11 | 35  30 | 32  28 |
| C | 48  4 | 47  3 | 42  13 | 32  34 | 26  32 | 27  12 |
| D | 47  7 | 44  10 | 32  37 | 25  36 | 24  11 | 30  0 |
| E | 47  3 | 35  33 | 28  27 | 26  20 | 21  12 | 28  0 |
| F |   |   | 36 | 25 |   |   |

METHOD AND APPARATUS FOR JUDGING AGGLUTINATION PATTERN

BACKGROUND OF THE INVENTION

The present invention relates to a method and an apparatus for judging an agglutination pattern in a diagnostic testing and, particularly, an apparatus for judging an agglutination pattern in an indirect passive agglutination method.

In an indirect passive agglutination method of immunological reactions i.e., the so-called microtiter method, measurements of very small amounts of immune components by detecting the presence or absence of an agglutination on a microplate have been used popularly. The presence or absence of the agglutination has been visually judged with naked eyes. In this judgement, a distibution of reactant in each well is obtained as an area of a portion having a light intensity lower than a predetermined value, it is compared with a reference positive agglutination pattern or a reference negative agglutination pattern, and/or the relationship of it to the states of adjacent wells is considered. Therefore, this method has such disadvantages that the visual judgement necessitates a high degree of skill, individual differences of judging exist due to a sensitive judging method, and reproducibility is generally poor.

An automation of this visual judgement by an apparatus can not only eliminate labor but also can largely improve the measuring accuracy. Although an agglutination reaction has merits such a number of testing items to be applied, a simple operation, a high sensitivity and a wide adaptation for processing a number of samples, it still has a disadvantage that the final judgement cannot be automated. Therefore, it is very important in a diagnostic testing to solve this disadvantage and to develop an accurate automatic judging method of the agglutination reaction so as to remarkably contribute to the medical developments and an apparatus for performing it.

However, it is sophisticated and economically expensive to visually judge an agglutination pattern by the same judgement in an equipment involving a combination of complicated factors which has been achieved at present, and lacks practicability. Thus, it is technically important to bring the judgement obtained by an automatic testing apparatus into coincidence with the visual judgement as precisely as possible while limiting the number of judging factors in the automatic judgement. Conventional automatic judging apparatuses which have been heretofore proposed employ photometers to make the light absorbance of a center of each well correspondent to an agglutination pattern or to make the ratio of an amount of light fallen around the center of a well to that fallen in the peripheral edge of the center of the well correspondent to an agglutination pattern. However, these apparatuses have been used as an auxiliary means of visual judgement, and there is no apparatus having compatible performance with visual judgement.

Since the conventional apparatus measures wells one by one, it is time consuming in measurements and needs means for moving a plate which has a number of wells.

The conventional automatic judging apparatus utilizes a transmission light, and samples of an agglutination reaction contain not only serum but also various proteins. These components are independently deposited from the agglutination reaction.

This phenomenon occurs in complicated combinations of sample serum and reagent solutions and becomes unignorable, particularly, when a long time has elapsed after the sample was mixed with reagent or protein and/or saline concentration is high. In the conventional apparatus, an amount of usable transmission light is significantly reduced due to random reflection of the light by a deposit. Thus, the amount of the transmission light and an agglutination reaction do not correspond to each other correctly, and an accurate judgement of the agglutination pattern is impossible in the conventional automatic agglutination judging apparatus of the type of a concentration into a light transmission conversion.

In the conventional apparatus, since transmission light is absorbed by reactant only once while passing vertically through a well, the resultant contrast tends to become turbid and unclear.

In order to eliminate the drawbacks of the above conventional apparatus, the present inventors have proposes a high speed apparatus for automatically judging agglutinations in a plurality of wells in a stationary microplate by arranging a TV camera and a light source on the same side of the microplate, and picking up the optical state of the microplate thereby (Japanese patent application No. 57880/1985).

This apparatus has a plate stand for placing the microplate, a TV camera and a light source arranged above the plate stand which includes an image input unit capable of reflecting transmission light passing through the microplate and an image processor for judging the agglutination state by processing an image signal inputted from the TV camera.

In this agglutination judging apparatus, the light source irradiates uniform light to respective wells of the microplate and hence diluted solutions in the wells. The intensity of light is selected such that a detectable range of reactant concentration when such turbidity exists coincides with that without turbidity. On the other hand, after passing through the diluted solution while being absorbed by the reactant, it is reflected by the bottoms of the wells or a reflecting plate arranged therearound, and passes again through the diluted solution while being again absorbed by the reactant. Therefore, the contrast of the image formed by light passing through the respective portions is intensified according to the concentration of the reactant. The light from the wells is picked up by the TV camera to obtain optical informations of all the wells. The optical informations are transmitted as an image signal from the TV camera to the image processor which processes the signal to judge the agglutination patern.

According to this apparatus, the influence of the turbidity is reduced to a satisfactory range. However, when the light amount in each well is intended to be increased to provide sufficient contrast only by the illumination from above, the power of the light source must be extremely increased, which causes heat generation to be increased. Thus, it is necessary to install a cooler such as a fan causing the apparatus to become complicated and expensive in addition to large power consumption. Since the dynamic range of the TV camera is limited, the light amount can be increased up to a level at which the brightness of the upper surface of the microplate becomes predetermined. In such case, the interiors of the wells cannot be sufficiently bright. Further, an image of the light source may appear on the liquid surface in the well which may be superposed with an agglutination image, causing the measurement to become sometimes difficult.

A conventional image processing method for processing the image signal from the TV camera in the image processor extracts only the image of an inputted object to be measured and measures the area, length of periphery, and angle of the extracted image and the number of the images. In a method of extracting an image to be measured, the extraction is performed by assigning an image having an intensity lower than a predetermined value to an intensity "0" and an image having an intensity higher than the value to the maximum intensity of the intensity range (binarizing process) when there is an intensity difference between the image to be measured and the other image. Or, it may be performed by extracting a profile of an image to be measured by differentiating a difference between the image to be measured and a background to obtain the gradient of the intensity, obtaining points of the largest gradient and connecting the points. However, it is necessary in these methods that an intensity difference clearly exists between the image to be measured and the other portion and that the light is uniform.

However, in order to satisfy these requirements, the apparatus becomes expensive of the judgement to be performed thereby must be compatible with the visual judgement because the factors to be used in such apparatus is limited in number to much smaller than that used in the visual judgement intentionally or not.

The method of extracting a profile of an image by differentiating an intensity difference is generally difficult. More specifically, the luminance of a portion in a well in which the agglutination pattern is formed is different between the agglutination pattern and the remaining disk-like portion of the periphery of the agglutination pattern since transmission light from below is interrupted by the agglutination pattern and light from above is less reflected thereby than the reflection from the microplate itself. Since a portion of the upper surface of the microplate in which there is no well is flat, light from below passing therethrough reaches the TV camera directly, and light from above is reflected and reaches the TV camera. On the other hand, since the edge of the well is obliquely lowered in shape, light from below is partly the reflected and reflected portion cannot reach the TV camera, and light from above is also reflected partially thereby resulting in some reduction of light to the TV camera. Therefore, an intensity difference occurs between the flat portion of the microplate and the edge of the well. Thus, in the judgement of the agglutination of the microplate, two edges of the agglutination pattern and the well are extracted as images. Further, if a defect exists inside the well, an intensity difference may appear in such defect. When a measuring item, a measuring date, and the number of plates are described on the upper surface of the microplate to distinguish this microplate from others, they are also extracted.

As described above, it has been difficult to accurately obtain an area of an agglutination pattern in a well by an image processing method known per se.

SUMMARY OF THE INVENTION

An object of the present invention is, therefore, to provide a method and an appratus for judging an agglutination pattern which can eliminate undesired factors caused by the problems mentioned above.

Another object of the present invention is to provide a method and an apparatus for judging an agglutination which can automatically judge the agglutination pattern with the same accuracy obtained by a skillful visual judging operator.

The present invention utilizes the fact that, for each well, an agglutination pattern is circular regardless of clearness of profile thereof, that luminance is the lowest at a center of the circle and becomes higher with a distance from the center, and that for the microplate, the distance between adjacent wells is constant.

When the central position of the well is determined, the profile of the agglutination pattern can be selectively extracted by differentiating luminance from the central position radially outwardly, detecting radial points at which the differential coefficient is maximum, and connecting these points. In order to maintain the positional relationship between the TV camera and the microplate physically constant, the apparatus must be composed of precision parts for positioning the microplate which causes the size and weight of the apparatus to be extremely increased. In addition, when a physical displacement occurs due to ageing change, the measuring accuracy becomes inaccurate.

Therefore, in the present invention, a positioning opening is formed at a base for placing a microplate, the coordinates of the opening are measured, and the central position of each well of the microplate and hence the central position of an agglutination pattern is thereafter determined from the coordinates, so that even if the relative position of the TV camera and the microplate is slightly displaced, the center of the agglutination pattern can be accurately obtained by calculation. This method is very important to reduce the size and the weight of the apparatus, and is effective to maintain the performance for a long period of time. The profile of the agglutination pattern is obtained by using the central position accurately obtained, and by detecting the points at which luminance changes from "dark" to "bright" with the maximum differential coefficient. Therefore, noise components can be remarkably reduced and thus the uniformity of the illumination of the apparatus is not always ncessary.

The agglutination judging apparatus according to the present invention has an image input unit including a light transmittable plate stand for placing a microplate, a light source and a TV camera provided to receive light from the microplate placed on the plate stand, and an image processor for processing an image signal inputted from the TV camera to judge the agglutination state. The plate stand is perforated to provide positioning openings for precisely positioning the wells of the microplate, and the image processor determines the central position of each well by light passing through the positioning opening and then divides the image of each well into a plurality of sectors to obtain, in each sector, a differential value of each picture element from a total of the luminance differences between the element and outward picture elements, compares the differential values of the picture elements in each direction, and counts the number of the picture elements in each radial direction having within two of those having largest values to obtain an area of the agglutination.

The image processor has a video input unit for receiving an output from the TV camera, a digital image memory for recording the data of picture elements, a video output unit for feeding the content of the memory to a computer as required, and a, microcomputer for processing the output of the video output unit, and further has a video input monitor TV, and a printer for recording the calculated result.

The image processor may divide radially the image of the well into at least into four or more segments, and the number of divisions may be increased as long as the differentiated value to be described later can be property determined. The intrinsic differential value to be determined for each picture element is a total of the values obtained by reducing a luminance value from luminance values of picture elements disposed outside the certain picture element. The picture elements disposed outside are suitably altered in number and disposition according to the number of segments and the position thereof.

The differential values of the respective picture elements are sequentially compared in one direction which may be horizontal, perpendicular or oblique.

The direction of light from the light source of the agglutination judging apparatus of the present invention may be arbitrary provided that it illuminates the wells of the microplate uniformly. The optical information supplied to the TV camera is transmitted as image signals to the image processor, which, in turn, differentiates luminance of the picture elements to find the edges of the agglutination portions, to count the picture elements between the edges and to compare them with a reference value.

DETAILED DESCRIPTION OF THE PREFERRED EMBODIMENTS

Figure 1:
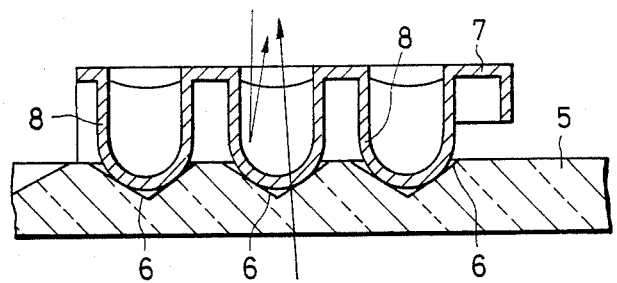
FIGS. 1 to 5 are views of a method of determining a profile of an agglutination used in a method of present invention.

A method of determining the edge of the agglutination will be described in more detail with reference to FIGS. 1 to 5. A plate stand 5 is formed of a transparent plastic, and its upper surface has, as shown in FIG. 1, substantially conical recesses 6 for receiving wells 8 of a microplate 7 at precise positions.

Figure 2:
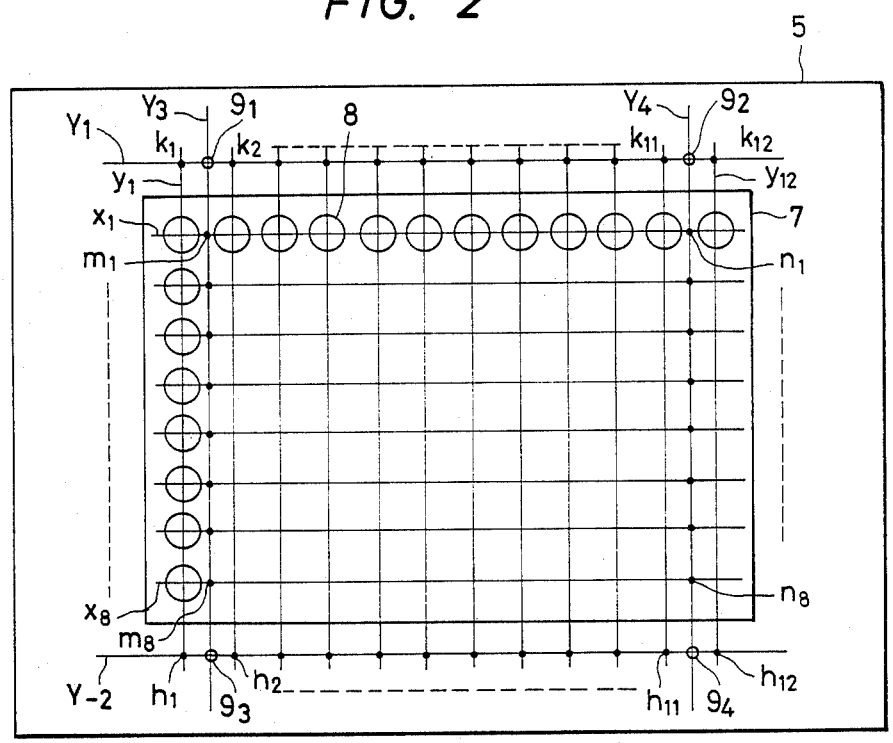

In FIG. 2, positioning openings 9 are perforated at the positions corresponding to vertexes of a rectangle and light passes through the plate stand 5 vertically upwardly.

A main light source (not shown) is provided above the plate stand 5. An auxiliary light source of less power than the main light source may be provided below the plate stand 5.

The coordinates of the positioning openings 9 are used to determine the central position of each well. In FIG. 2, assuming that the positions of the positioning openings are at coordinates of $9_1(x_1,y_1)$, $9_2(x_2,y_2)$, $9_3(x_3,y_3)$ and $9_4(x_4,y_4)$, a line connecting the positioning openings $9_1$ and $9_2$ is expressed by $Y_1=a_1x+b_1$. Similarly, three linear lines $Y_2$, $Y_3$ and $Y_4$ connecting the positioning openings $9_3$ and $9_4$; $9_1$ and $9_3$ and $9_2$ and $9_4$ are obtained, respectively and totally four linear lines are thus obtained.

Then, the linear lines $Y_1$ and $Y_2$ are divided into 11 equal segments, respectively, to obtain 12 dividing points $k_1 \ldots k_{12}$ and $h_1 \ldots h_{12}$. Then, 12 lines $y_1, \ldots y_{12}$ connecting horizontally these points are obtained, respectively.

Further, dividing points $m_1, \ldots m_8$ and $n_1, \ldots n_8$ of the remaining linear lines $Y_3$ and $Y_4$ are obtained, and 8 linear lines $x_1, \ldots x_8$ for connecting these points are obtained.

Then, the crossing points of linear lines $y_1, \ldots y_{12}$ and linear lines $x_1, \ldots x_8$ are obtained, which are used as the centers of the wells.

Figures 3, 4:
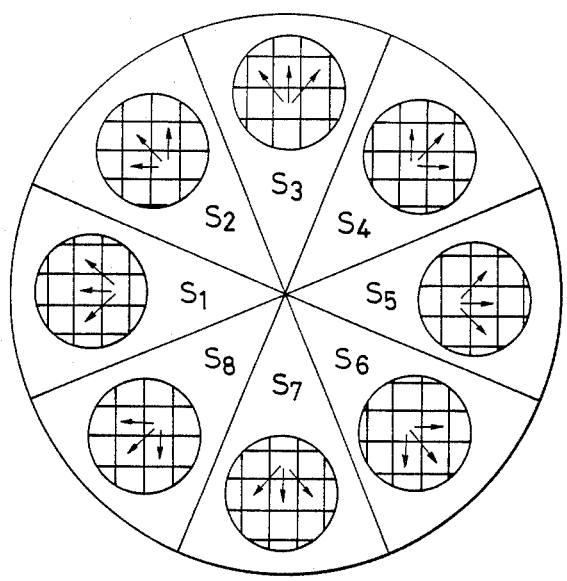

As shown in FIG. 3, an image of each well is divided radially into 8 sectors $S_1, S_2, \ldots, S_8$, and the differential values of the picture elements in the sectors $S_1, \ldots S_8$ are determined respectively. The differential value of each picture element is a total of differences in luminance between the picture element and adjacent three respective picture elements disposed radially outwardly of the picture element in question. In the sector $S_1$, picture elements disposed adjacent to the left side, oblique upper left side and oblique lower left side of a picture element are to be compared in luminance with the latter and a total of differences are to be determined as the differential value of the picture element in question. In the sector $S_2$, picture elements disposed adjacent to the upper side, left side and oblique upper left side of a picture element are compared in luminance with the latter and a total of differences are to be determined as a differential value thereof, and so on.

FIG. 4 illustrates the differential values of the picture elements of the sector $S_2$. In FIG. 4, symbols A to F and numerals I to VI designate the rows and columns of the sector and the number attached to the upper left of each picture element indicates intensities. For example, when the differential value of the picture element D-III having an intensity of "32" is considered, a differential value of this picture element is 37 because the intensities of picture elements D-II, C-II and C-III outwardly surrounding the element D-III are respectively "44", "47" and "42", i.e., 12 $(=44-32)+15$ $(=47-32)+10$ $(=42-32)=37$. Thus, the differential value of each picture element is determined.

Figures 5, 6, 9:
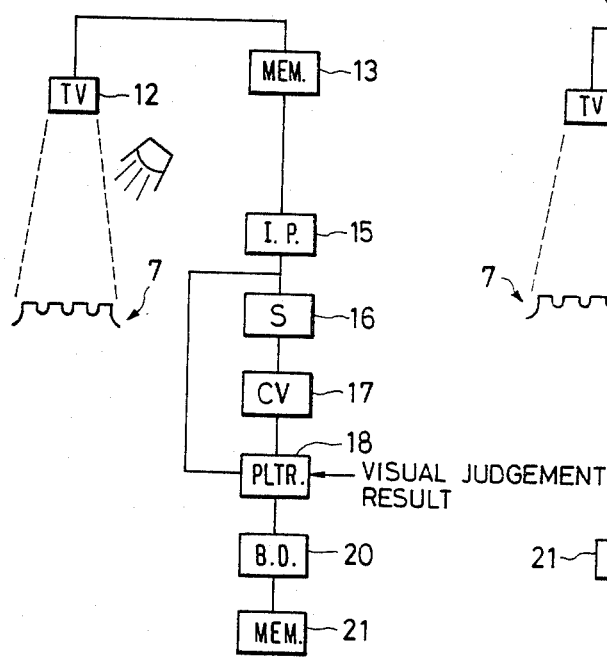
FIG. 6 is a view of a construction of an apparatus for determining a criterion in a method of the present invention.
FIG. 9 is a schematic diagram of an apparatus for judging according to the criterion.

When the differential values of the respective picture elements are determined, the differential values of the picture elements aligned on one line ae compared with each other to detect two picture elements having the largest two values in the same line as defining the edge of the agglutination. That is, when differential values are given as shown in FIG. 5, two picture elements in, for example, line d which have the largest value 38 are determined as defining the edge and, in line f, the picture elements having values 34 and 33 are detected as defining the edge. Similarly, when the edges are selected for all the lines the entire edge becomes as designated by a thick solid line in FIG. 5. In FIG. 5, dotted chain lines indicate the actual edges of the agglutination portion. The number of picture elements inside the edge are counted, and the area of the agglutination is compared with a reference value.

This is very effective to limit the profile of the differential image. However, it is still indluenced by the contrast of the original image. As described above, the contrast becomes blurred due to types and lots of reagent, variation in an optical system including a light source, and variations of blood solution.

As described above, it is indispensable in the accurate agglutination judgement to completely remove variation of the contrast of image over a number of agglutination images.

According to the present invention, the distribution of picture elements having a luminance level not zero is considered with the aid of a microcomputer. A standard deviation of the distribution is obtained and is divided by a mean luminance level to obtain a variation coefficient CV. Since the CV does not contain factors due to variation of contrast, the problem caused thereby can be completely removed. The CV values obtained in this manner are plotted in the area (number of the picture elements) to obtain a distribution for special items, and the judged results by the skillful visual judging operators for the same items are superposed on the CV distribution to determine the boundary of judgement, which is stored in a computer memory. Another agglutination image for the same items and area are similarly obtained, which are compared with data in the computer memory and judged automatically according to positions of the CV values thereof on the area.

In detail, the standard deviation S is obtained by the following equation, where the picture element having an intensity level of zero or higher in the differential image is designated by Xi.

$$S = \sqrt{\frac{\Sigma X i^2 - \frac{(\Sigma X i)^2}{n}}{n}}$$

where n is the number of picture elements.

The CV value is obtained by the following equation:

$$CV = \frac{S}{\bar{x}} \times 100$$

where $\bar{x}$ is value of intensity level.

This CV is not affected by variation of contrast.

At least a plurality of agglutination images are prepared for a specific agglutination reaction and original video images thereof are differentiated by the abovementioned method to determine its profile. The areas and the CV values thereof are obtained as described above, and the CV values are, for example, plotted on an ordinate axis, and the area are plotted on an abscissa axis in an orthogonal coordinate system. Simultaneously, the same agglutination images are judged by at least a plurality of skillful visual judging operators, and the results of the visual judgements are superposed on the pattern to define the regions where positive and negative patterns exist. The positive and negative regions exist adjacently to each other, partly overlapped. The regions can be separated by a linear line drawn such that the overlapped portion is minimized and this linear line is used as a boundary between positive and negative agglutination regions, which are stored in a memory as reference data of the specific agglutination reaction. Thereafter, similar plottings for the agglutination images which are not processed for visual judgement, are compared with the stored reference to determine their positive or negative patterns. Thus, the judgements having high correlation with the results of the visual judgements can be conducted irrespective of the contrast of the original image.

EXAMPLE 1

FIG. 6 is a schematic view of an apparatus for performing a method according to the present invention. In FIG. 6, an agglutination image on a microplate 7 is stored as a suitably illuminated video image in a TV camera 12 having an image memory 13, and the stored video image is differentiated as a differential image, then an area of the profile of the image is obtained by an image processor 15.

The standard deviation S of a picture element whose intensity level is zero or higher is obtained by a standard deviation calculator 16 from the obtained profile and the area of the image, and its CV is further obtained by a CV calculator 17. This CV is applied to a plotter 18 together with the area obtained by the image processor 15, and is plotted on a graph having, for example, an ordinate as CV and an abscissa as the area. This process is executed for a number of samples and CV and the areas of the images are stored as patterns on the graph.

The same agglutination image is judged by a plurality of visual judging operators, and the judged results are inputted to the plotter 18 to be superposed on the pattern on the graph. As a result, the patterns on the graph are partly superposed to be divided into positive and negative patterns.

A linear line for dividing the positive and negative with minimized overlapping region is determined by a boundary determining device 20, and is stored in a memory 21.

Figure 7:
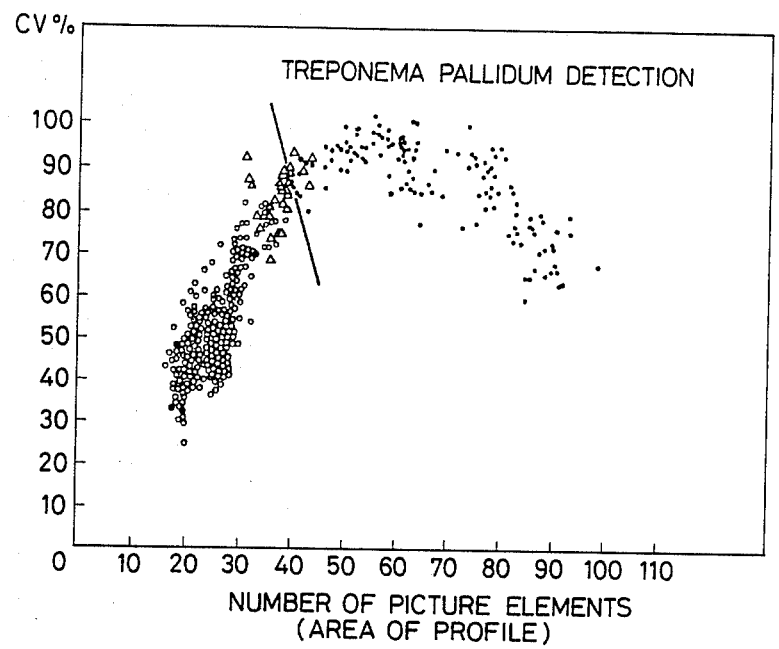
FIG. 7 is a diagram of a criterion of detecting a Treponema Pallidum antibody obtained by the apparatus of FIG. 6.
Figure 8:
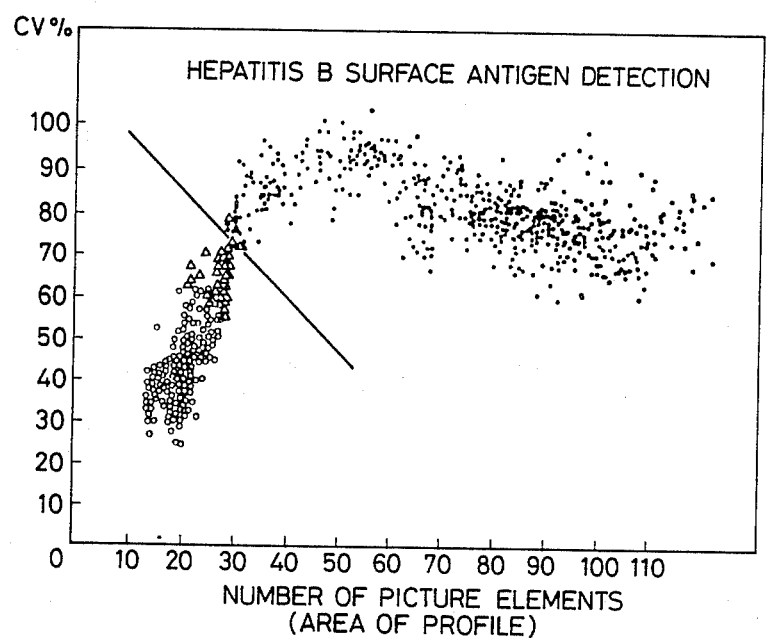
FIG. 8 is a diagram of a criterion of detecting hepatitis B surface antigen obtained by the apparatus of FIG. 6.

FIG. 7 shows the results of hem agglutination reaction with Treponema pallidum antibody (TP) as testing item obtained by processing 800 samples to be considered to have suitable potencies by using "SERODIA TP" (manufactured by Fujirebio Inc.). FIG. 8 shows the similar results of hepatitis B surface antigen using "SERODIA HBs" (manufactured by Fujirebio Inc., Japan). In FIGS. 7 and 8, the agglutination images judged as positive by the visual judgement are plotted with "●", the agglutination images judged as negative by the visual judgement are plotted with "O", and overlaps are marked with "Δ". The partitioning with the linear line by the boundary determining device 20 is preferably executed on the region including plots "Δ" to minimize the region. In other words, the inclination of a linear line should be selected according to the distribution pattern empirically.

The automatic judgement of the agglutination reaction by the judging criterion stored will be described with reference to FIG. 9. In FIG. 9, the agglutination images from a TV camera 12 are stored in an image memory 13, and are processed by an image processor to decide their areas, the areas are plotted by a plotter 18 together with CVs obtained by a standard deviation calculator 15 and a variation coefficient calculator 17, and compared with the criterion stored in the memory 21 by a comparator 22 as in FIG. 6 to judge whether the agglutination is positive or not.

The above-mentioned operation will be executed in terms of testings.

Coincidence rate and reproducibility of detecting hepatitis B surface antigen (HBs) and Treponema pallidum antibody (TP) obtained by executing ten times the abovedescribed operation for 800 samplees are listed in next Table.

| Testing | Coincidence rate with visual judgement (%) | Coincidence rate with visual judgement (within 1 well difference) (%) | Simultaneous reproducibility |
|---------|---------|---------|---------|
| HBs | 88.6 | 100.0 | 0.993 |
| TP | 89.4 | 100.0 | 0.972 |

From the above Table, it is understood that the criterion according to the present invention and the visual judgement by the skillful judging operator remarkably coincide. A satisfactory reproducibility is also shown.

Constructive details of the apparatus of the present invention can be readily understood by those skilled in the art. The apparatus shown in FIGS. 6 and 9 can be readily integrated or partially shared.

According to the present invention as described above, the agglutination can be judged entirely without influence of the variation of contrast of the agglutination image, and can also be rapidly operated. Further, the accuracy of the judgement can be reliably maintained at least in the judging accuracy obtainable by the skillful visual judging operator.

What is claimed is:

1. A method of judging an agglutination pattern comprising the steps of:
   setting a reference value, and
   judging the testing agglutination pattern,
   said reference value setting step including the steps of:
   (a) storing video images of a plurality of agglutination images,
   (b) differentiating the video images to produce differential images;
   (c) producing an area of the profile of the differential images;
   (d) producing a variation coefficient of each picture element of a differential image having a luminance level not zero from a standard deviation of the picture elements,
   (e) plotting the relationship between the variation coefficients and the area of the profile,
   (f) inputting a visual judgement of a plurality of agglutination images to plot the images on a plot of said relationship,
   (g) determining a linear line on the relationship plot so that an overlapping portion of positive and negative agglutination regions of the plot of the visual judgement on the plot of said relationship is obtained, and
   (h) storing the result obtained from step (g) of determining the linear line, and
   said agglutination judging step including the steps of:
   (i) executing the above steps (a) to (e) for independently prepared agglutination images, and
   (j) comparing the result obtained in step (i) with the linear line stored in step (h).

2. The method as claimed in claim 1, wherein step (b) comprises the steps of dividing said video image into a partition of sectors and determining a difference in brightness between each picture element of said video image in each sector and other picture elements disposed radially outwardly of said each picture element.

3. The method as claimed in claim 1, wherein step (c) comprises assigning a first and a second picture element arranged in each horizontal scanning line, which have two most significant values of difference, as those constituting the profile.

4. An apparatus for judging an agglutination, comprising: a plate stand which is light transmittable for placing a microplate and perforated with positioning openings for positioning a central position of each well of the microplate, a light source disposed to illuminate the plate stand, a TV camera provided for light irradiated from above the microplate placed on the plate stand to be incident, an image memory for storing an output image of the TV camera, a processor for differentiating the stored image to determine the profile of the image, a counter for counting picture elements having intensity levels larger than zero of the differentiated image, means for producing a coefficient of variation, a plotter for producing the relationship between the coefficient of variation from the output of the counter and the counted value, and a comparator for comparing the output of the plotter with a reference value.

5. The apparatus as claimed in claim 4, wherein said processor and said counter determine the central position of each well by the light transmitted through the positioning openings, then divide the image of each well into a plurality of picture elements radiating outwardly from the central position, differentiate the value totalized from the difference of the intensities of outward picture elements in the divided portions as the differentiated value of each picture element, sequentially compare the differential values of the picture elements, and count the number of picture elements between two most significant differential values.

* * * * *